United States Patent
Agrawal et al.

(10) Patent No.: US 11,339,104 B2
(45) Date of Patent: May 24, 2022

(54) PROCESS FOR UPGRADING NATURAL GAS LIQUIDS FROM SHALE GAS WITHOUT FRONT-END DEMETHANIZER

(71) Applicant: PURDUE RESEARCH FOUNDATION, West Lafayette, IN (US)

(72) Inventors: Rakesh Agrawal, West Lafayette, IN (US); Yiru Li, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 16/831,993

(22) Filed: Mar. 27, 2020

(65) Prior Publication Data

US 2020/0308088 A1     Oct. 1, 2020

Related U.S. Application Data

(60) Provisional application No. 62/847,234, filed on May 13, 2019, provisional application No. 62/826,313, filed on Mar. 29, 2019.

(51) Int. Cl.
*C07C 5/333* (2006.01)
*C07C 2/06* (2006.01)
*C10L 3/10* (2006.01)
*C10G 5/00* (2006.01)
*C07C 11/02* (2006.01)

(52) U.S. Cl.
CPC ............ *C07C 5/333* (2013.01); *C07C 2/06* (2013.01); *C10L 3/102* (2013.01); *C10L 3/106* (2013.01); *C07C 11/02* (2013.01); *C10G 5/00* (2013.01)

(58) Field of Classification Search
None
See application file for complete search history.

(56) References Cited

U.S. PATENT DOCUMENTS

RE34,189 E  *  3/1993  Harandi ................... C07C 2/00
                                                        208/64
2010/0313754 A1*  12/2010  Okada ................ B01D 53/228
                                                        95/56
(Continued)

FOREIGN PATENT DOCUMENTS

WO     2019/051101     3/2019

OTHER PUBLICATIONS

Sinnott, "Chapter 2 Fundamentals of Material Balance", Coulson & Richardson's Chemical Engineering—Chemical Engineering Design, vol. 6, Fourth Edition, 2005, pp. 34-35. (Year: 2005).*

(Continued)

*Primary Examiner* — Philip Y Louie
(74) *Attorney, Agent, or Firm* — Edmonds & Cmaidalka, P.C.

(57) ABSTRACT

Processes and systems for upgrading natural gas liquids. At least a portion of the natural gas liquid components in a shale gas stream can be dehydrogenated to their corresponding olefin derivatives prior to separating any methane from the liquids. Further processing subsequent to dehydrogenation could include various separations, oligomerizing olefins produced in the dehydrogenation step, recovering desired products, etc. The order of the processing steps subsequent to dehydrogenation could be adjusted in various cases.

20 Claims, 9 Drawing Sheets

(56) References Cited

U.S. PATENT DOCUMENTS

| | | |
|---|---|---|
| 2015/0157998 A1 | 6/2015 | Luebke et al. |
| 2015/0158786 A1 | 6/2015 | Mertens et al. |
| 2015/0158791 A1* | 6/2015 | Keusenkothen .......... C07C 1/06 526/348 |
| 2019/0039972 A1* | 2/2019 | Schoonebeek ............ C07C 5/48 |

OTHER PUBLICATIONS

International Search Report and Written Opinion for International Application No. PCT/US2020/025123, dated Jun. 19, 2020.

* cited by examiner

PROCESS FOR UPGRADING NATURAL GAS LIQUIDS FROM SHALE GAS WITHOUT FRONT-END DEMETHANIZER

CROSS-REFERENCE TO RELATED APPLICATIONS

This application claims priority to U.S. Provisional Patent Application having Ser. No. 62/826,313, filed on Mar. 29, 2019, and Ser. No. 62/847,234, filed on May 13, 2019. The entirety of both are incorporated by reference herein.

GOVERNMENT LICENSE RIGHTS

This invention was made with government support under Cooperative Agreement No. EEC-1647722 awarded by the National Science Foundation. The government has certain rights in the invention.

BACKGROUND OF THE INVENTION

Field of the Invention

Embodiments provided herein relate to systems and processes for converting paraffins (saturated hydrocarbons) to olefins (unsaturated hydrocarbons). More particularly, such embodiments relate to systems and processes where natural gas liquid components within shale gas stream are dehydrogenated prior to separating methane from the natural gas liquids.

Description of the Related Art

More efficient utilization of petroleum and gas reserves is an important strategy for the deployment of future energy generation. Shale gas has become an increasingly important source of natural gas in the United States, and the U.S. government's Energy Information Administration predicts that by 2050, nearly 90% of the United States' natural gas production will come from tight and shale resources. Many of these shale gas formations contain wet gases, which can include substantial concentrations of natural gas liquids (NGL). NGL is a mixture of hydrocarbons constituting primarily ethane, propane, butane, and pentane.

Current elevated levels of gas development have lifted NGL production to an all-time high, leading to concerns over NGL processing and distribution in the coming years. Several major shale gas formations such as the Marcellus and Bakken are located far away from historically gas producing and processing regions, such as the Gulf Coast. These resources can be considered as stranded gas. Construction of pipelines to transport natural gas liquids to large, existing processing plant complexes, such as those located along the Gulf Coast, can be capital intensive. This creates an opportunity to upgrade this stranded gas, particularly its condensate, or NGL, for further processing as it is easier to distribute to the market.

Table 1 below shows a typical shale gas composition from wells at Barnett, Eagle Ford and Bakken fields. It is worth noting that methane is the predominant component of a shale gas stream, and is much greater than 50 mol %. The combined mole fraction of all the NGL components (i.e., C2, C3, C4 and C5+ alkanes) varies from 5 mol % to 45 mol %.

TABLE 1

Typical shale gas compositions from wells at Barnett, Eagle Ford and Bakken fields.

| Species | Mole Percentage (mol %) | | |
|---|---|---|---|
| | Barnett | Eagle Ford | Bakken |
| $CH_4$ | 85 | 74 | 58 |
| $C_2H_6$ | 6 | 14 | 20 |
| $C_3H_8$ | 2 | 5 | 11 |
| $C_4H_{10}$ | 2 | 3 | 4 |
| $C_{5+}$ | 0 | 2 | 1 |
| $N_2$ | 2 | 0 | 4 |
| $H_2O$ | 0.26 | 0.28 | 0.29 |
| $CO_2$ | 2 | 1 | 1 |
| $H_2S$ (mg/scf) | 335 | 307 | 115 |

Currently, raw shale gas pipelined from a reservoir or wellheads first passes through an acid gas removal unit where the acid components, such as $CO_2$ and $H_2S$ are removed. The sweetened gas coming out of the acid gas removal then typically passes through a dehydration unit to get rid of any water vapor. Any nitrogen in the shale gas might also be removed after the dehydration step. After acid gas removal and dehydration, a sweet and dry shale gas is obtained, and primarily includes methane and NGLs. The NGLs in the sweet and dry shale gas are then separated from methane. Typically, methane and NGLs are separated in a distillation column, or demethanizer, which is operated cryogenically. The obtained NGL stream can be sent to various units for further processing. The current processing procedure for sweet and dry shale gas, including $CH_4/C_{2+}$ separation and further NGL processing, is shown in FIG. 1, which is a block flow diagram illustrating the foregoing processing steps. A few commercialized technologies are available for upgrading NGLs to liquid hydrocarbons, such as the UOP Cyclar™ process, Synfuels International ETG (Ethane to Gasoline), and Greyrock Direct Fuel Production™.

FIG. 2 is an example of the prior art referred in FIG. 1. Note that although not shown in the figure, the recovered NGL stream can be either a single NGL stream containing a mixture of $C_2$-$C_5$ alkanes or multiple streams each containing ethane, propane, butane and pentane, respectively, which are obtained by passing the NGL stream through a series of distillation columns, or fractionation train. The NGLs are dehydrogenated to their corresponding olefins and possibly sent to further processing units. Currently, ethane recovered from NGL is almost exclusively used for ethylene production via steam cracking (dehydrogenation); propane used for petrochemical feedstock is dehydrogenated to propylene via processes such as UOP Olefex.

FIG. 2 is another block flow diagram showing the conventional processing steps (i.e. prior art) for converting natural gas liquids where a sweet and dry shale gas is first removed of methane and the separated NGLs are sent for dehydrogenation and further processing. FIG. 3 is yet another block flow diagram showing the conventional processing steps (i.e. prior art) for converting natural gas liquids where a sweet and dry shale gas is first removed of methane and the separated NGLs are processed using a two-step catalytic dehydrogenation and oligomerization process for the production of liquid hydrocarbons.

Referring to FIG. 3, methane is removed to a low concentration in stream 20 through a separation system 110, consisting of any suitable separation scheme such as a typical cryogenic NGL extraction process, distillation and/or membrane technology. The separated methane stream 21 is then used as a fuel gas or sold as a product via a pipeline. After methane removal, the methane-poor feed 20 is sent to a dehydrogenation unit 120 to produce alkenes such as ethylene, propylene, butylene, etc. Stream 20 is combined with a recycle stream 62, which is predominantly unconverted ethane, propane, ethylene, butylene, and residual hydrogen from the back end processing. The combined stream 22 is then passed to a dehydrogenation reactor 120. Hydrogen is then removed from the dehydrogenator effluent and the alkenes in the effluent are oligomerized and separated into various product slates 60 using conventional distillation or other separation techniques. A purge stream 63 is used to avoid the build-up of methane in the recycle loop 62.

However, in all the technologies mentioned above, including cracking ethane to ethylene, dehydrogenation of propane to propylene, and converting NGLs to liquid hydrocarbons, NGLs are first separated from methane before any upgrading. Separation of methane from ethane, propane and butane prior to the downstream processing such as dehydrogenation is deemed essential.

There is a need, therefore, for new systems and processed for upgrading natural gas liquids without removing methane prior to the conversion of the alkanes to alkenes.

SUMMARY

A process for converting natural gas liquids wherein at least a portion of the processing steps towards natural gas liquids, such as alkane dehydrogenation to alkene, takes place prior to the separation of methane, and the possible remaining processing steps are subsequent to the methane separation unit.

A process for converting natural gas liquids comprises providing a sweet and dry shale gas stream, dehydrogenating at least a portion of the NGL components contained in the shale gas stream prior to separating any methane from the NGLs, separating the exiting stream from dehydrogenation unit to desired one or more product streams containing dehydrogenated alkenes for further downstream processing.

A process for converting natural gas liquids comprises providing a sweet and dry shale gas stream, dehydrogenating at least a portion of the NGL components contained in the shale gas stream prior to separating any methane from the NGLs, separating the exiting stream from dehydrogenation unit to desired one or more product streams of alkenes as well as majority of the hydrogen formed during dehydrogenation and recycling unconverted ethane, propane, butane and pentane to the dehydrogenation unit.

The temperature of the stream entering the dehydrogenation may be between 550-900° C. The dehydrogenation may use catalyst or cracking without catalyst. The separation of the stream exiting the dehydrogenation may employ any feasible distillation column configuration or membrane system. The hydrogen formed in the dehydrogenation unit may be left mixed with methane or alternatively, some of the hydrogen may be separated and collected as a $H_2$-rich stream. Methane and hydrogen may be separated through distillation or membrane.

A process for converting natural gas liquids comprises providing a sweet and dry shale gas stream, dehydrogenating at least a portion of the NGL components contained in the shale gas stream prior to separating any methane from the NGLs, separating methane and hydrogen from the stream exiting the dehydrogenation, oligomerizing olefins to higher molecular hydrocarbons, recovering liquid hydrocarbons and recycling unconverted ethane, propane, butane, pentane and their olefin counterparts to the dehydrogenation unit.

A process for converting natural gas liquids comprises providing a sweet and dry shale gas stream, dehydrogenating at least a portion of the NGL components contained in the shale gas stream prior to separating any methane from the NGLs, removing a portion of the hydrogen formed in the dehydrogenation unit and contained in the stream exiting the dehydrogenation unit, oligomerizing olefins produced from the dehydrogenation to higher molecular hydrocarbons, recovering higher molecular hydrocarbons as liquid hydrocarbons, separating methane and the remaining hydrogen, and recycling unconverted ethane, propane, butane, pentane and their olefin counterparts to the dehydrogenation unit.

A process for converting natural gas liquids comprises providing a sweet and dry shale gas stream, dehydrogenating at least a portion of the NGL components contained in the shale gas stream prior to separating any methane from the NGLs, oligomerizing olefins produced from the dehydrogenation to higher molecular hydrocarbons, recovering higher molecular hydrocarbons as liquid hydrocarbons in a two-stage separation, separating methane and the remaining hydrogen, and recycling unconverted ethane, propane, butane, pentane and their olefin counterparts to the dehydrogenation unit.

A process for converting natural gas liquids comprises providing a sweet and dry shale gas stream, dehydrogenating at least a portion of the NGL components contained in the shale gas stream prior to separating any methane from the NGLs, oligomerizing olefins produced from the dehydrogenation to higher molecular hydrocarbons, recovering higher molecular hydrocarbons as liquid hydrocarbons in a two-stage separation, delivering the gas stream coming out of the first stage, containing methane and hydrogen, to the pipeline, and recycling the gas stream coming out of the second stage, containing unconverted ethane, propane, butane, pentane and their olefin counterparts to the dehydrogenation unit.

A process for converting natural gas liquids comprises providing a sweet and dry shale gas stream, dehydrogenating at least a portion of the NGL components contained in the shale gas stream prior to separating any methane from the NGLs, oligomerizing olefins produced from the dehydrogenation to higher molecular hydrocarbons, recovering higher molecular hydrocarbons as liquid hydrocarbons in a two-stage separation, separating at least a part of the hydrogen from the gas stream coming out of the first stage, delivering the remaining stream coming out of the hydrogen separation unit to pipeline, and recycling the gas stream coming out of the second stage, containing unconverted ethane, propane, butane, pentane and their olefin counterparts to the dehydrogenation unit.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. It is emphasized that the figures are not necessarily to scale and certain features and certain views of the figures can be shown exaggerated in scale or in schematic for clarity and/or conciseness.

The accompanying drawings are incorporated into and form a part of the specification to illustrate aspects and examples of the present disclosure. These figures together with the description serve to explain the general principles of the disclosure. The figures are only for the purpose of illustrating examples of how the various aspects of the disclosure can be made and used and are not to be construed as limiting the disclosure to only the illustrated and described examples.

DETAILED DESCRIPTION

Figure 1:
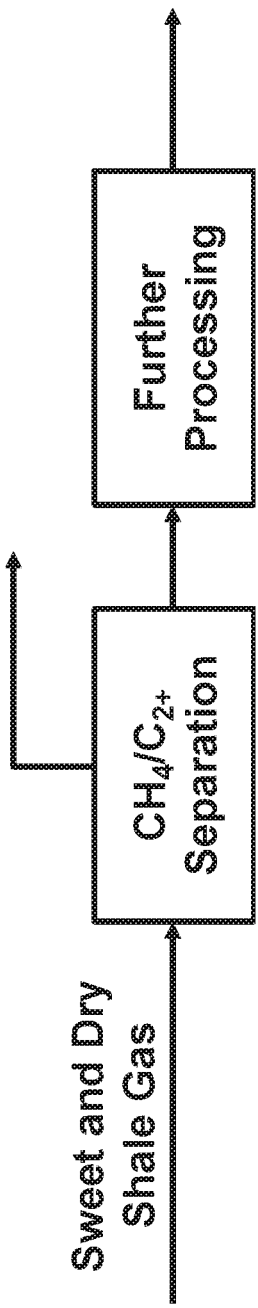
FIG. 1 is a block flow diagram showing the conventional processing steps (i.e. prior art) for converting natural gas liquids where a sweet and dry shale gas is first removed of methane and the separated NGLs are sent for further processing.
Figure 2:
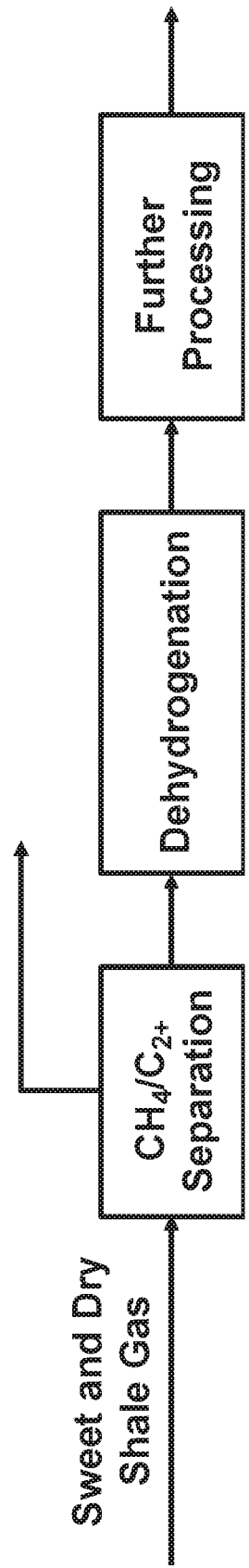
FIG. 2 is another block flow diagram showing the conventional processing steps (i.e. prior art) for converting natural gas liquids where a sweet and dry shale gas is first removed of methane and the separated NGLs are sent for dehydrogenation and further processing.

Each of the appended claims defines a separate invention, which for infringement purposes is recognized as including equivalents to the various elements or limitations specified in the claims. Depending on the context, all references to the "invention" may in some cases refer to certain specific embodiments only. In other cases, it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this disclosure is combined with publicly available information and technology.

It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure can repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. The exemplary embodiments presented below also can be combined in any combination of ways, i.e., any element from one exemplary embodiment can be used in any other exemplary embodiment, without departing from the scope of the disclosure.

Additionally, certain terms are used throughout the following description and claims to refer to particular components. As one skilled in the art will appreciate, various entities can refer to the same component by different names, and as such, the naming convention for the elements described herein is not intended to limit the scope of the invention, unless otherwise specifically defined herein. Further, the naming convention used herein is not intended to distinguish between components that differ in name but not function.

The terms "including" and "comprising" are used in an open-ended fashion, and thus should be interpreted to mean "including, but not limited to." The phrase "consisting essentially of" means that the described/claimed composition does not include any other components that will materially alter its properties by any more than 5% of that property, and in any case, does not include any other component to a level greater than 3 wt %.

The term "or" is intended to encompass both exclusive and inclusive cases, i.e., "A or B" is intended to be synonymous with "at least one of A and B," unless otherwise expressly specified herein.

The indefinite articles "a" and "an" refer to both singular forms (i.e., "one") and plural referents (i.e., one or more) unless the context clearly dictates otherwise.

The term "acid gases" refers to $CO_2$ and sulfur containing compounds, such as $H_2S$, contained in raw shale gas.

The terms "alkane" and "paraffin" are used interchangeably and both refer to any saturated molecule containing hydrogen and carbon atoms only, in which all the carbon-carbon bonds are single bonds and are saturated with hydrogen. Such saturated molecules can be linear, branched, and/or cyclic.

The terms "alkene" and "olefin" are used interchangeably and both refer to any unsaturated molecule containing hydrogen and carbon atoms only, in which one or more pairs of carbon atoms are linked by a double bond. Such unsaturated molecules can be linear, branched, or cyclic, and can include one, two, three or more pairs of carbon atoms linked by double bounds (i.e. mono-olefins, di-olefins, tri-olefins, etc).

The terms "$CH_4$ containing stream" and "methane containing stream" both refer to a stream containing more than 50 mol % methane ($CH_4$).

The terms "$CH_4$ rich stream" and "methane rich stream" are used interchangeably and both refer to a stream containing more than 90 mol % methane ($CH_4$).

The term "hydrocarbon" refers to an organic compound that contains only hydrogen and carbon atoms. The term "$C_n$" hydrocarbon wherein n is a positive integer, e.g., 1, 2, 3, 4, or 5 or more, means a hydrocarbon molecule having n number of carbon atom(s) per molecule. The term "$C_{n+}$" hydrocarbon means a mixture of hydrocarbons containing at least one hydrocarbon having n carbon atoms and at least one hydrocarbon having more than n carbon atoms.

The terms "hydrocarbon gas" or "gas feed" are used interchangeably and both refer to any gaseous mixture that naturally contains methane and one or more other hydrocarbons. Illustrative gas mixtures can be or can include a raw shale gas stream or raw natural gas stream or other raw hydrocarbon stream that is obtained directly (i.e. without processing to remove water and/or acid gas) from a reservoir, wellhead, or pipeline. Suitable gas mixtures can also originate from a refinery, such as from a FCC, coker, steam cracker, and pyrolysis gasoline (pygas). Suitable gas mixtures can also be or can include coal gas. Illustrative gas mixtures can also be or can also include a gas that has been treated for acid gas and water removal. For simplicity and ease of description, the detailed description provided herein makes specific references to "shale gas" or "natural gas" or "dry shale gas" or "sweet and dry shale gas"; however, those same references equally apply to any gas mixture containing at least 50 mol % methane and at least 5 mol % NGL, regardless of how or where the gas mixture is obtained.

The terms "hydrogen rich stream" and "$H_2$ rich stream" are used interchangeably and both refer to a stream containing more than 90 mol % hydrogen ($H_2$).

The term "liquid hydrocarbon" refers to a hydrocarbon that is liquid at room temperature and ambient pressure, and primarily includes $C_{5+}$ hydrocarbons. Moreover, this term can also refer to hydrocarbons that are liquid at room temperature but require high pressure such $C_4$ alkane and alkenes.

The term "natural gas liquid" or "NGL" refers to the $C_{2+}$ alkanes originally contained in a natural gas or shale gas stream, which primarily includes ethane, propane, butane and pentane.

The term "NGL alkene derivative" refers to any one or more $C_{2+}$ alkenes derived from the dehydrogenation of NGL. Illustrative NGL alkene derivatives can be or can include one or more olefins having from about 2 to about 12 carbon atoms or more. Illustrative NGL alkene derivatives can also be or can also include one or more linear alpha olefins, such as ethene, propene, butenes, pentenes and/or hexenes.

The terms "olefin derivative" and "alkene derivative" used interchangeably and refer to any unsaturated hydrocarbon that has the same carbon arrangement as another saturated hydrocarbon. The only difference between a saturated hydrocarbon and its olefin derivative or alkene derivative is the double bond.

The term "oligomer" refers to dimers, trimers, tetramers, and other molecular complexes having less than 26 repeating units. Oligomers provided herein are typically gases or liquids at ambient temperature, and can include low melting solids, including waxes, at ambient temperature. In some embodiments, the oligomers provided herein can have an atomic weight or molecular weight of less than 10,000 AMU (Da), such as about 5,000 or less, 1,000 or less, 500 or less, 400 or less, 300 or less, or 200 or less. The molecular weight of the oligomer, for example, can range from a low of about 50, 250 or 350 to a high of about 500, 3,000, 7,000, or 9,000 AMU (Da).

The term "oligomerization" refers to the formation of an oligomer from molecules of lower relative molecular mass. Any suitable oligomerization system and process can be used. The process can be carried out, for example, in a continuous stirred tank reactor, batch reactor, plug flow reactor, or bubble column reactor. One or more reactors operated in series or parallel can be used. The process can be operated at partial conversion to control the molecular weight of the product and unconverted olefins can be recycled for higher yields. Further, once the catalyst is deactivated with high molecular weight carbon, or coke, it can be regenerated using known techniques in the art, including for example, by combustion in air at a temperature of about 400° C. or higher.

The term "raw shale gas" refers to shale gas that is pipelined from reservoirs or wellheads prior to any further processing.

The term "shale gas" refers to natural gas that is produced from a shale or other tight formation, which is a gaseous phase mixture containing natural gas liquids, acid gases, water, nitrogen ($N_2$), and possibly trace amounts of contaminants. A suitable shale gas (or natural gas) contains at least 50 mol % $CH_4$ and up to 45 mol % of $C_2H_6$, $C_3H_8$, $C_4H_{10}$, and/or $C_{5+}$ hydrocarbons. For example, a suitable shale gas (or natural gas) contains about 60 mol % to about 95 mol % $CH_4$ and about 5 mol % to about 40 mol % of $C_2H_6$, $C_3H_8$, $C_4H_{10}$, and/or $C_{5+}$ hydrocarbons (or collectively referred to as "$C_{2+}$ hydrocarbons" or "$C_{2+}$ alkanes"). Among the $C_{2+}$ hydrocarbons, $C_2H_6$ is generally the highest concentration followed by $C_3H_8$ then $C_4H_{10}$. Nitrogen gas (Na) can also be present in the shale gas.

The term "sweet and dry shale gas" refers to shale gas obtained after acid gases and water have been removed from the raw shale gas. Insignificant amounts of other components in the sweet shale gas can be removed together with water and thus, a sweet and dry shale gas has almost all the components contained in raw shale gas except acid gases and water. Since acid gases and water can be in relatively small concentration, the composition of the sweet and dry shale gas is similar, or substantially the same, as that of the raw shale gas.

The term "sweet shale gas" refers to shale gas obtained after the acid gases have been removed from the raw shale gas. Insignificant amounts of other components in the raw shale gas can be removed together with acid gases and thus, a sweet shale gas has almost all the components contained in raw shale gas except acid gases.

The term "wt %" means percentage by weight, "vol %" means percentage by volume, "mol %" means percentage by mole, "ppm" means parts per million, and "ppm wt" and "ppmw" are used interchangeably and mean parts per million on a weight basis. All concentrations herein, unless otherwise stated, are expressed on the basis of the total amount of the composition in question.

The following detailed description illustrates embodiments of the present disclosure. These embodiments are described in sufficient detail to enable a person of ordinary skill in the art to practice these embodiments. It should be understood, however, that the embodiments and examples described herein are given by way of illustration only, and not by way of limitation, the embodiments are chosen and described so that others skilled in the art may appreciate and understand the principles and practices of the present teachings. Various substitutions, modifications, additions, and rearrangements can be made that remain potential applications of the disclosed processes. Therefore, the description that follows is not to be taken as limiting on the scope of the appended claims. In particular, an element associated with a particular embodiment should not be limited to association with that particular embodiment but should be assumed to be capable of association with any embodiment discussed herein.

It has been surprisingly discovered that converting natural gas liquids to its alkene derivatives in the presence of large amounts of methane is more economical and improves conversion rates. The presence of methane in the dehydrogenation reaction lowers the partial pressure of the NGLs, which surprisingly and unexpectedly, pushes the dehydrogenation reaction to higher conversion rates. It has also been surprisingly and unexpectedly discovered that methane can serve as a thermal mass in the dehydrogenation reaction, which can significantly reduce operating costs. Methane separation, after dehydrogenation, can be easily combined with NGL fractionation, which significantly reduces capital and operating expenses, not to mention significantly reducing the size and spacing of the various unit operations.

Figure 4:
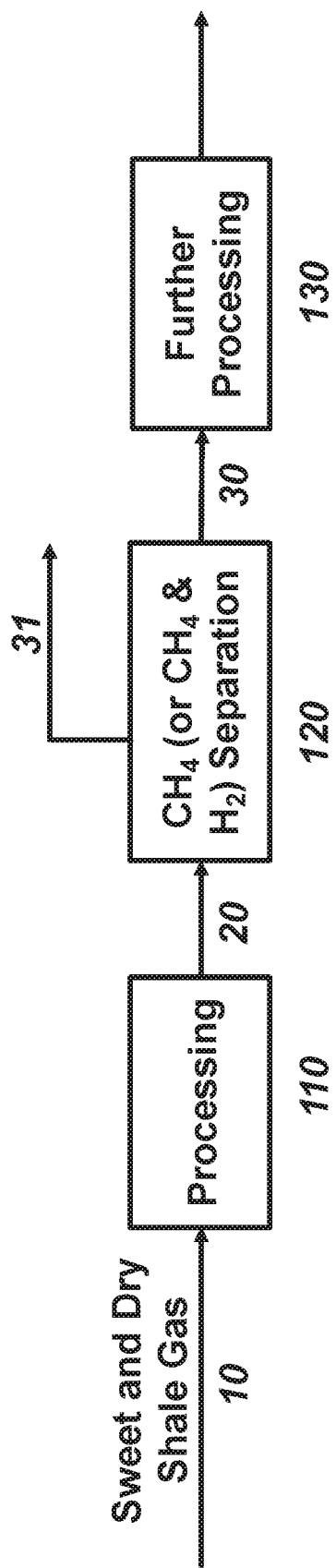
FIG. 4 depicts a flow diagram of an illustrative process for processing a hydrocarbon stream prior to methane separation, according to one or more embodiments provided herein.

FIG. 4 depicts a flow diagram of an illustrative process for processing a hydrocarbon stream prior to methane separation, according to one or more embodiments provided herein. As depicted, a hydrocarbon gas stream or gas feed stream 10 containing a large amount methane and other NGLs can be processed in one or more procession units 110 to provide an effluent stream 20. The processing unit 110 can be used to convert at least a portion of the NGLs in the gas feed 10 to one or more olefinic molecules, such as $C_2$-$C_5$ alkenes and higher alkenes, depending on the feed composition. The processing unit 110 can be a single processing unit or multiple processing units arranged in parallel or series. For example, the processing unit 110 can be a dehydrogenation reactor. The processing unit 110 can also include a series of processing units including a dehydrogenation reactor, a hydrogen separation membrane and an oligomerization reactor.

The effluent stream 20 can then enter one or more methane and/or hydrogen separators 120. The separation unit 120 can be or can include any one or more distillation or membrane systems where methane is separated from the $C_{2+}$ hydrocarbons. At the same time, any hydrogen and/or nitrogen in the stream 20 can also be removed together with methane in stream 31. The exiting stream 30 from the separation unit 120 can then be further processed in unit 130, if necessary. The further processing units 130 are further described below with reference to the embodiments depicted in FIGS. 5-11.

Considering the gas feed 10 in more detail, the gas feed 10 can be any hydrocarbon stream. For example, the gas feed 10 can be a sweet and dry shale gas that is obtained by passing raw shale gas pipelined from a reservoir or one or more wellheads through one or more acid gas removal and dehydration units. Acid gas and water removal helps to protect downstream equipment and improves overall performance of downstream processing, such as catalyst operation and separation devices.

The range of compositions for raw shale gas from different fields in the USA is shown in Table 1 below. Since acid gases $H_2S$ and $CO_2$, and water are in relatively small concentration, the composition of the gas feed 10 will generally be similar to that of a raw shale gas. The gas feed 10 can also have at least 50 mol % methane and up to 40 mol % of a mixture of ethane, propane and $C_{5+}$ hydrocarbons. The gas feed 10 can also include 70 mol % to 95 mol % methane and anywhere from about 5 mol % to about 30 mol % $C_{2+}$ hydrocarbons. Among the $C_{2+}$ hydrocarbons, ethane will generally be in the highest concentration followed by propane then butane. Some nitrogen may also be present in the shale gas (i.e. less than 5 mol %).

In certain embodiments, the amount of methane in the gas feed 10 can be at least 25 mol %, at least 30 mol %, at least 33 mol %, at least 35 mol %, at least 40 mol %, at least 45 mol %, at least 50 mol %, at least 55 mol %, at least 60 mol %, at least 65 mol %, or at least 75 mol %. The gas feed 10, for example, can include 30 mol % to 95 mol % methane; 35 mol % to 95 mol % methane; 30 mol % to 90 mol %, or 50 mol % to 90 mol %. The gas feed 10 also can include methane ranging in amounts from a low of about 30 mol %, about 33 mol %, or about 35 mol % to a high of about 55 mol %, about 75 mol %, or about 95 mol %.

In certain embodiments, the amount of $C_{2+}$ hydrocarbons in the gas feed 10 can be at least 5 mol %, at least 6 mol %, at least 7 mol %, at least 8 mol %, at least 10 mol %, at least 20 mol %, at least 25 mol %, at least 30 mol %, at least 33 mol %, at least 35 mol %, or at least 45 mol %. The gas feed 10, for example, can include $C_{2+}$ hydrocarbons in amounts of about 5 mol % to 45 mol %; 10 mol % to 45 mol %; 15 mol % to 45 mol %, or 5 mol % to 35 mol %. The gas feed 10 also can include of $C_{2+}$ hydrocarbons ranging in amounts from a low of about 5 mol %, about 10 mol %, or about 15 mol % to a high of about 30 mol %, about 35 mol %, or about 40 mol %.

Figure 5:
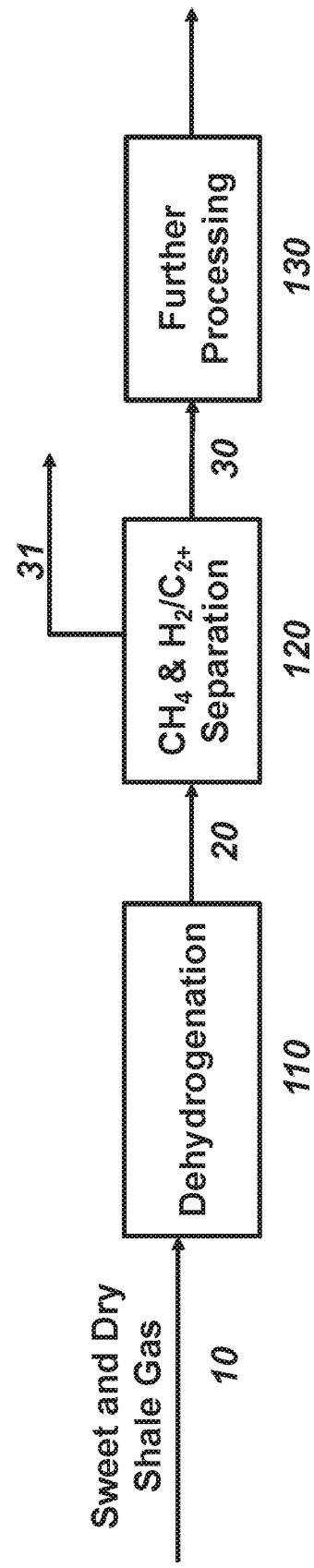
FIG. 5 depicts a flow diagram of another illustrative process for processing a hydrocarbon stream using a dehydrogenation reactor prior to methane separation, according to one or more embodiments provided herein.

FIG. 5 depicts a flow diagram of another illustrative process for processing a hydrocarbon stream using a dehydrogenation reactor 110 prior to methane removal, followed by possible further processing steps. The process shown in FIG. 5 is similar to the process shown in FIG. 4. In the process of FIG. 5, however, the processing units 110 are one or more dehydrogenation reactors 110. The dehydrogenation reactor 110 can operate at any temperature between about 550° C. and 950° C., and at any pressure between about 1 bar and 30 bars. The operating temperature and pressure can change to meet any design specifications.

The conversions of $C_2$-$C_5$ alkanes to their alkene derivatives are endothermic and limited by their thermodynamic equilibrium. The heavier hydrocarbons have a greater propensity to dehydrogenate at lower temperatures. Although not shown in FIG. 5, heat is generally provided to the dehydrogenation reactor to increase olefin formation. In the dehydrogenation reactor(s) 110, the dehydrogenation reaction of NGLs might proceed without catalyst. Steam cracking and thermal cracking in absence of a catalyst are possible ways of achieving dehydrogenation of NGLs. Alternatively, catalytic dehydrogenation may be used to convert the alkanes to alkenes within the reactors 110. Depending on the technology pathway chosen for dehydrogenation and the composition of NGLs, the temperature and pressure of the dehydrogenation reactors 110 may might be adjusted accordingly.

The stream 20 exiting the dehydrogenation unit 110 can contain a mixture of methane, olefins, unconverted alkanes (NGLs), and hydrogen. The stream 20 can be fed to the separation unit 120, as described above with reference to FIG. 4, where methane can be separated from the other heavier hydrocarbons via stream 31. Stream 30 exiting the separation unit 120 is methane lean and contains the heavier hydrocarbons from stream 20.

In certain embodiments, the separation unit 120 can be or can include one or more distillation columns and the output from the dehydrogenation reactor (stream 20) can be sent to one or more demethanizer distillation column(s) (not shown). The column overhead can provide a methane-rich stream 31 containing byproduct hydrogen from the dehydrogenation reactor 110. A bottoms stream 31 from a demethanizer distillation column can include the $C_{2+}$ hydrocarbons from the stream 20. These $C_{2+}$ hydrocarbons are a mixture of one or more alkanes and one or more alkenes which is further sent for downstream processing in unit 130. The methane-rich stream 31 containing hydrogen can be either directly sold as a product or further processed to separate a hydrogen-rich stream. This further processing could be done either using distillation or a suitable membrane process or an adsorption-based process. If nitrogen is present in the gas feed 10, it will show up in stream 31, and if needed, this nitrogen could also be separated from the methane stream.

In certain embodiments, a bottoms stream (not shown) from a demethanizer distillation column can be further separated into two or more hydrocarbon streams. In one case, a $C_{2+}$ stream can be separated into a $C_2$ stream and a $C_{3+}$ stream. The $C_2$ stream can contain ethylene and any unreacted ethane. The $C_{3+}$ stream can contain the alkanes and alkenes with three or more carbon atoms. Each of the streams can then be sent for further processing in unit 120. It is also possible to further separate the $C_{3+}$ stream into two or more streams. For example, the $C_{3+}$ stream can be separated into a $C_3$ (propane and propylene) stream and a $C_{4+}$ stream. Similar separations can be continued with the $C_{4+}$ stream.

In certain embodiments, the $C_2$ stream can be further separated into an ethylene and an ethane stream and each one can be processed downstream as separate streams or sold as feed materials. Similarly, the $C_3$ stream could be further separated into a propylene stream and a propane stream. A similar treatment could be given to a $C_4$ stream. Such separations can be done using any combination of distillation columns and/or membranes.

In certain embodiments, water can be removed from the gas feed 10 prior to the dehydrogenation unit 110 using any suitable water removal techniques. In certain embodiments, water need not be removed. For example, if steam cracking is the dehydrogenation technique of choice in the dehydrogenation unit 110, there is no need to dry the gas feed 10 prior to the dehydrogenation step.

Figure 6:
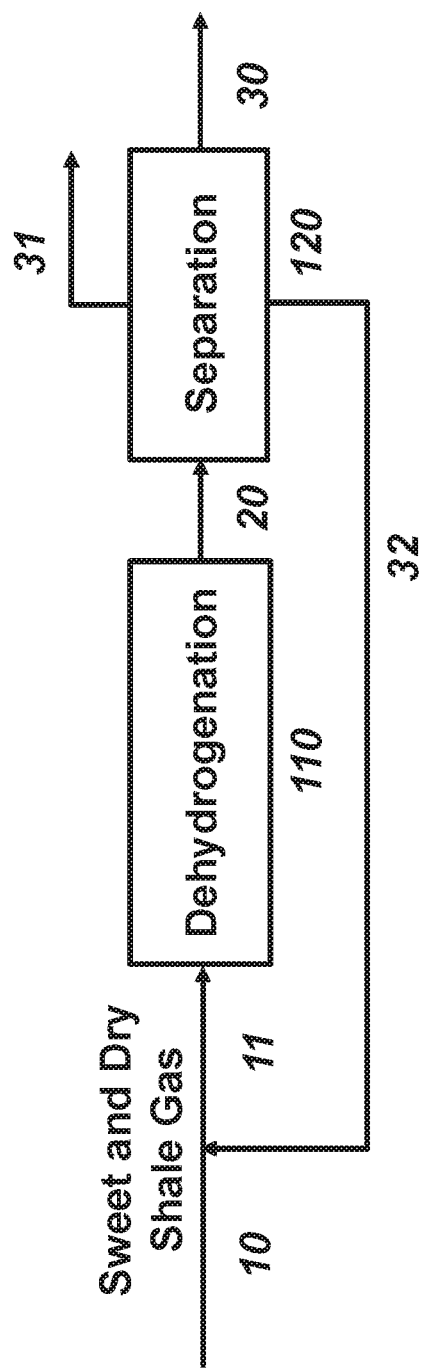
FIG. 6 depicts a flow diagram of another illustrative process for processing a hydrocarbon stream through a dehydrogenation reactor, the methane contained in the feed gas and hydrogen formed in the dehydrogenation unit are then separated in a separation unit, and the exiting stream passes through one or more further separation units to recover desired products. Optionally, unconverted components can be recycled, if desired.

FIG. 6 depicts a flow diagram of another illustrative process for processing a hydrocarbon stream through a dehydrogenation reactor, the methane contained in the feed gas and hydrogen formed in the dehydrogenation unit are then separated in a separation unit, and the exiting stream passes through one or more further separation units to recover desired products. This system and process is similar to that of FIG. 5 except that any unreacted alkane hydrocarbons that are separated or otherwise recovered in the separation unit 120 can be recycled to the dehydrogenation reactor 110 via stream 32. The subsequent separation unit 120 deploys option 3 described above, wherein ethylene, propylene, ethane, propane and $C_{4+}$, are all separated as independent streams. Ethylene, propylene and $C_{4+}$ can be pipelined as products, respectively, or sent for further processing. Unreacted ethane and propane can be recycled via stream 32 to the gas feed 10. The mixture of the gas feed 10 and recycle stream 32 can be combined as stream 11 and sent to dehydrogenation reactor 110.

Figure 7:
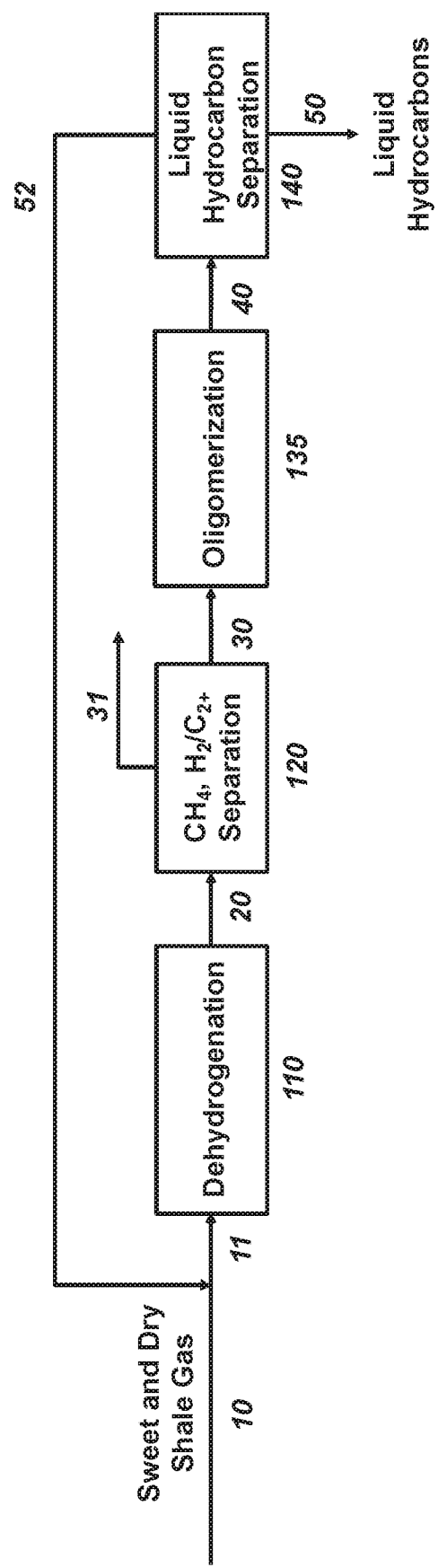
FIG. 7 depicts a flow diagram of another illustrative process where a hydrocarbon stream first passes through a dehydrogenation reactor, the methane contained in the gas and hydrogen formed in the dehydrogenation unit are separated and the exiting stream passes through an oligomerization unit, the liquid hydrocarbons are recovered from the oligomerization exhaust stream, and the remaining gas stream is recycled to the dehydrogenation unit.

FIG. 7 depicts a flow diagram of another illustrative process where a hydrocarbon stream first passes through a dehydrogenation reactor, the methane contained in the gas and hydrogen formed in the dehydrogenation unit are separated and the exiting stream passes through an oligomerization unit, the liquid hydrocarbons are recovered from the oligomerization exhaust stream, and the remaining gas stream is recycled to the dehydrogenation unit. Referring to FIG. 7, stream 30 exiting the separation system 120 can contain a mixture of olefins and unconverted NGLs. Stream 30 can then be introduced to one or more oligomerization reactors or systems 135 where the olefins in stream 30 can be converted to one or more oligomers.

The oligomerization reactor 135, for example, can operate at a relatively lower temperature (200° C. to 600° C.) and medium pressure (1 bar to 50 bar). The typical operating pressure ranges from about 5 bar to about 30 bar and the operating temperature typically ranges from about 100° C. to about 300° C. The stream 40 exiting the oligomerization reactor 135 can contain a mixture of $C_2$-$C_9$ hydrocarbons with a majority of the higher molecular weight hydrocarbons being greater than $C_6$, and preferably $C_{10}$-$C_{18}$, or even more carbon atoms. Stream 40 containing the oligomers can then be passed through the liquid hydrocarbon separation system 140, as described herein above. Stream 50 exiting the liquid hydrocarbon separation system 140 can contain one or more liquid hydrocarbons. The liquid hydrocarbons contained in stream 50 can be then be separated and collected as product streams. The vapor stream 52 exiting the separation system 140 can be or can include a mixture of unreacted light alkanes and light alkenes, especially ethane, ethylene, propane, propylene, butane and butylene. Stream 52 can be recycled and combined with the gas feed 10 to be passed to the dehydrogenation reactor 110. This recycle stream 52 adds the additional benefit of reducing the overall loss of NGLs, as compared to purging this stream, and thus increases the overall conversion of NGLs to liquid hydrocarbons.

Figure 8:
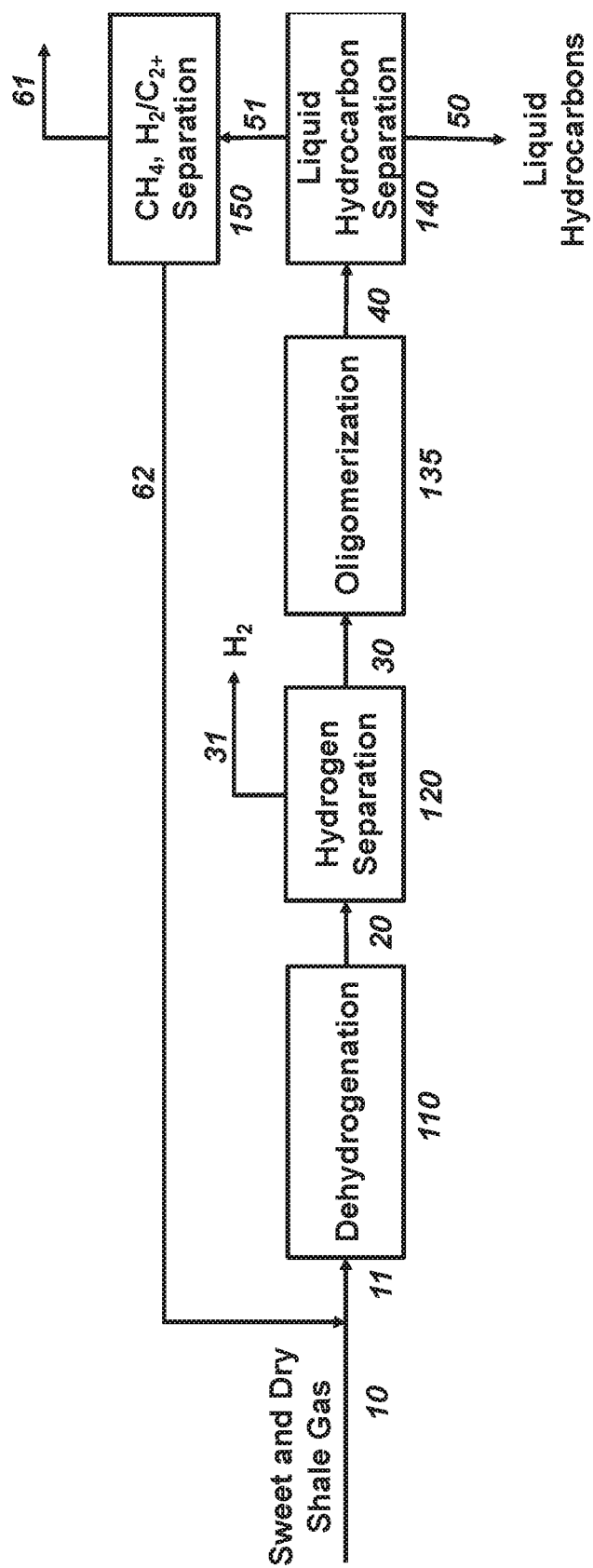
FIG. 8 depicts a flow diagram of another illustrative process where a hydrocarbon stream passes through a dehydrogenation reactor followed by hydrogen separation and an oligomerization reactor, the liquid hydrocarbons are recovered as product, and the remaining gas stream is further processed in a separation unit whereby methane and hydrogen are separated from other hydrocarbon components which are recycled to the dehydrogenation unit.

FIG. 8 depicts a flow diagram of another illustrative process, according to one or more embodiments provided herein. In FIG. 8, the stream 20 exiting the dehydrogenation reactor 110 contains a mixture of methane, olefins, unconverted NGLs, and hydrogen. Depending on the hydrogen tolerance of the downstream processes, some portion of the hydrogen might be first removed from stream 20 using a hydrogen separation system 150. Any suitable hydrogen separation system 150 can be used, including any one or more or any combination of distillation columns, strippers, and membranes. A sufficient amount of hydrogen 31 can be removed from the process to have only a residual concentration (i.e. less than 1 wt %, or less than 500 ppmw or less than 200 ppmw) of hydrogen in stream 30, which may be needed to ensure catalyst stability and mass balance in the oligomerization reactor 135. The hydrogen separation system 150 should possess high selectivity to hydrogen such that the losses of other components are minimized. Alternatively, if the oligomerization catalyst can tolerate high hydrogen concentration (i.e. more than 200 ppmw or more than 500 ppmw or more than 1 wt %), the hydrogen separation unit 120 can be eliminated.

The stream 30 exiting the hydrogen separation system 150 can be delivered to an oligomerization reactor 135 as described above. The stream 40 exiting the oligomerization reactor 135 containing a mixture of $C_2$-$C_9$ hydrocarbons with a majority of the higher molecular weight molecules being greater than $C_6$ hydrocarbons, and preferably $C_{10}$-$C_{18}$, or higher molecular weight can pass through the liquid hydrocarbon separation system 140.

The vapor stream 51 coming out of the liquid hydrocarbon separation system 150 can contain a mixture of methane, hydrogen, unconverted light alkanes and light alkenes, which are gas at ambient temperature and pressure. The stream 51 exiting the separation system 140 can be delivered to a methane separation unit 150 where methane and hydrogen can be separated via stream 61. Stream 61 can be further separated to recover methane and hydrogen separately, if needed, using conventional methodologies known in the art.

Stream 62 exiting the separation system 150 can contain a mixture of unreacted light alkanes and light alkenes, especially ethane, ethylene, propane, propylene, butane and butylene. Stream 62 can be recycled and combined with gas feed 10 to be passed to the dehydrogenation reactor 110. Alternatively, the separation system 150 can be a less rigorous separation system and stream 61 might contain more $C_{2+}$ alkanes and alkenes. Stream 51 can also be directly used as a fuel gas or a pipeline gas as long as this stream meets the composition requirement for the pipeline gas, and if needed, its BTU value can be adjusted by adding an inert diluent gas such as nitrogen.

Figure 9:
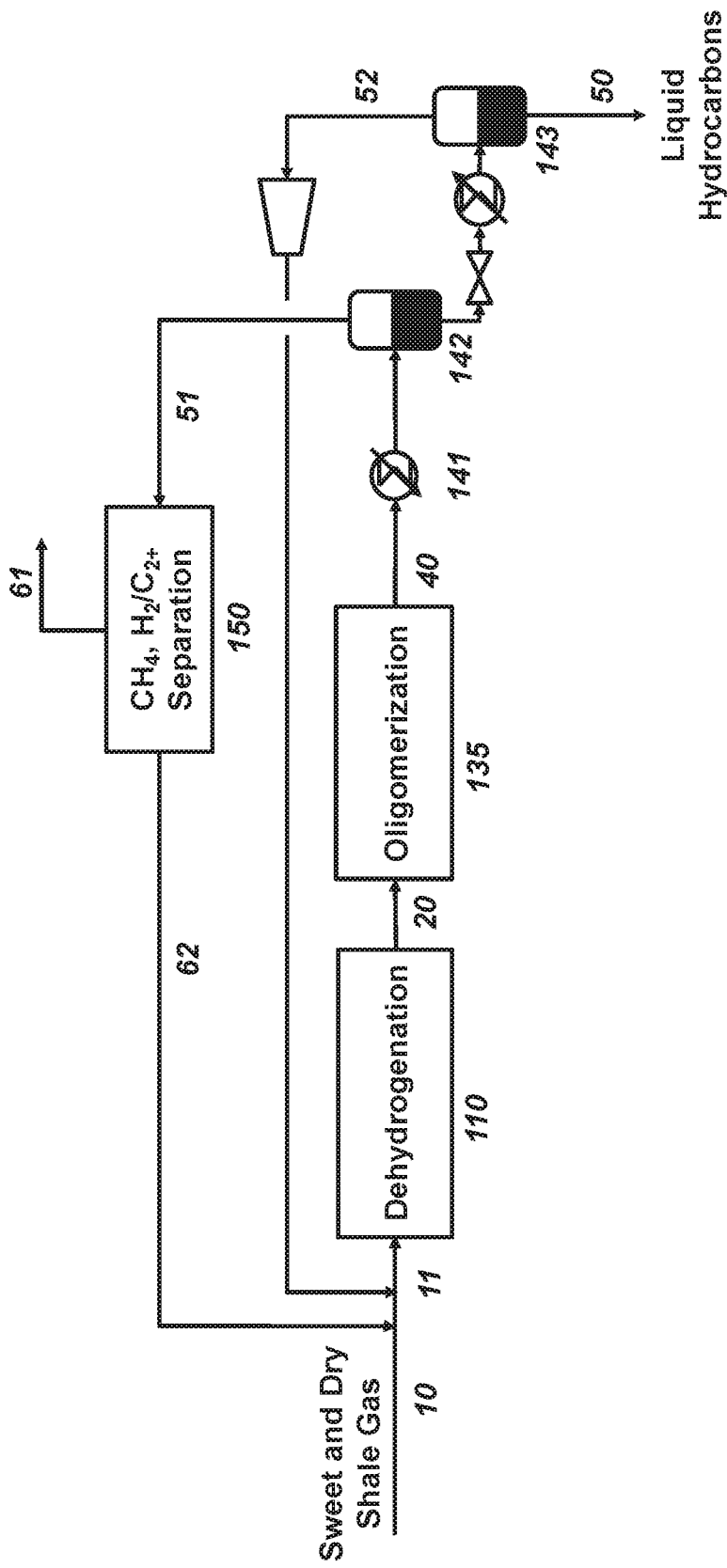
FIG. 9 depicts a flow diagram of another illustrative process where a hydrocarbon stream passes through a dehydrogenation reactor followed by an oligomerization reactor, the liquid hydrocarbons are recovered as product via a two-stage flash separation, and the remaining gas stream is further processed in a separation unit whereby methane and hydrogen are separated from other hydrocarbon components which are recycled to the dehydrogenation unit.

FIG. 9 depicts a flow diagram of yet another illustrative process, according to one or more embodiments provided herein. FIG. 9 is an extension and modification of FIG. 8. In FIG. 9, the stream 20 existing the dehydrogenation unit 110 directly enters an oligomerization reactor 135 without prior hydrogen separation. An oligomerization catalyst that can tolerate the hydrogen presence should be used. Such catalysts are known in the art and are commercially available. Stream 40 existing the oligomerization reactor 135 is similar to that shown in previous embodiment but will contain more hydrogen. Stream 40, for example, can contain at least 1 mol %, at 2 mol %, at least 3 mol %, at 4 mol %, at least 5 mol %, or at least 6 mol % hydrogen. Stream 40 can then be cooled via heat exchanger 141 and delivered to a separator 142 to condense the liquid hydrocarbons contained in the stream. The gas stream 51 existing the separator 142 can contain mostly methane and hydrogen, with some unconverted light alkanes and light alkenes. Stream 51 can be delivered to a methane separation unit 150 where methane and hydrogen are separated in stream 61, which can be subsequently separated to provide a methane rich stream and a hydrogen rich stream. Stream 62 exiting the separation system 150 can contain a mixture of unreacted light alkanes and light alkenes, especially ethane and propane. Stream 62 can be recycled and combined with gas feed 10 to be passed to the dehydrogenation reactor 110.

The liquid stream exiting the separator 142 can be expanded to ambient pressure, heated to ambient temperature, and delivered to a second flash separator 143 to recover more light alkanes and light alkenes. The liquid stream 50 exiting the flash separator 143 is recovered as liquid hydrocarbon product. The gas stream 52 exiting the flash separator 143 mainly contains a mixture of unreacted light alkanes and light alkenes, especially ethane, ethylene, propane, propylene, butane and butylene. Stream 52 can be recycled and combined with gas feed 10 to be passed to the dehydrogenation reactor 110, thereby further increasing NGL conversions.

Figure 10:
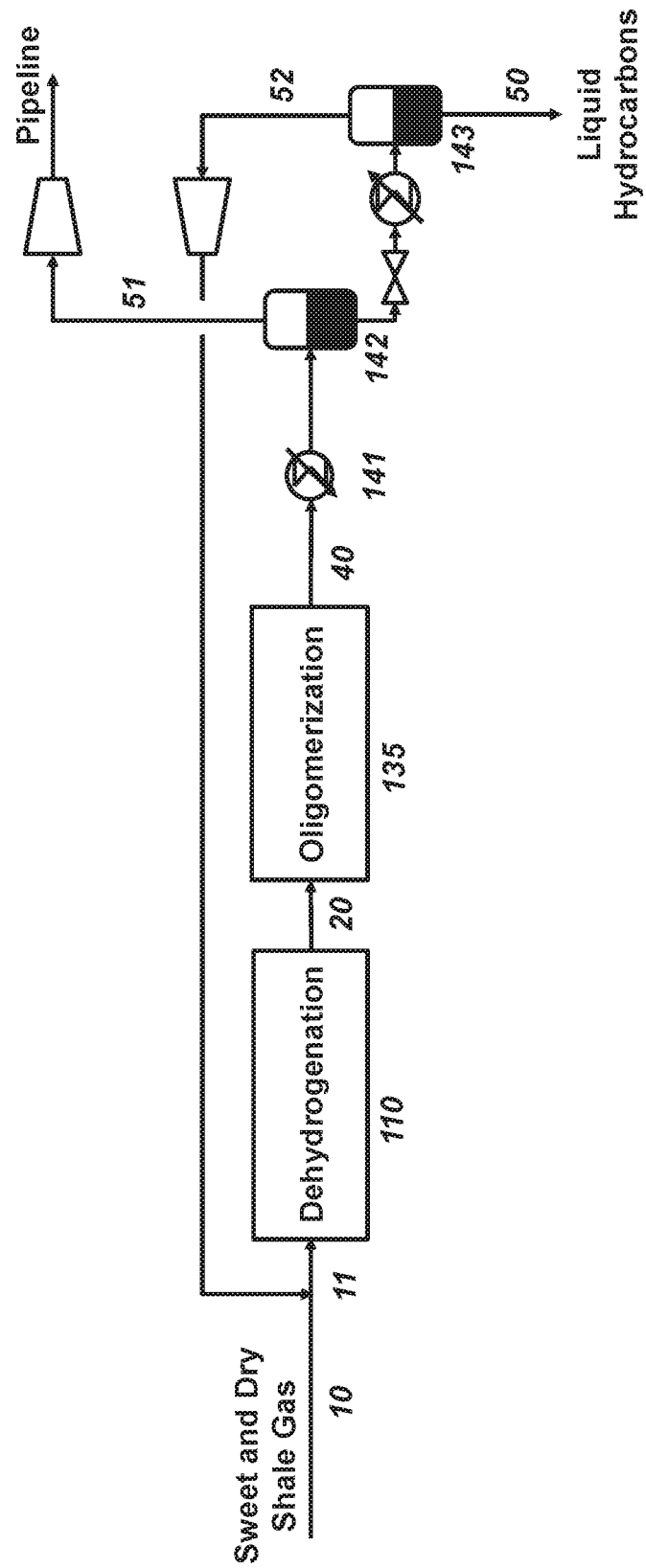
FIG. 10 depicts a flow diagram of another illustrative process where a hydrocarbon stream passes through a dehydrogenation reactor followed by an oligomerization reactor, the liquid hydrocarbons are recovered as product via a two-stage flash separation, the remaining gas stream is partially delivered to the pipeline and a part of the gas is recycle to the dehydrogenation unit.

FIG. 10 depicts a flow diagram of yet another illustrative process, according to one or more embodiments provided herein. FIG. 10 illustrates an alternative process to that in FIG. 9. Instead of entering a separation system 150 to separate methane and hydrogen, the stream 51 exiting the flash separator 142 can be directly sent to a pipeline. FIG. 10 largely simplifies the process by eliminating the methane and hydrogen separation system 150 and the associated recycle stream 62.

Figure 11:
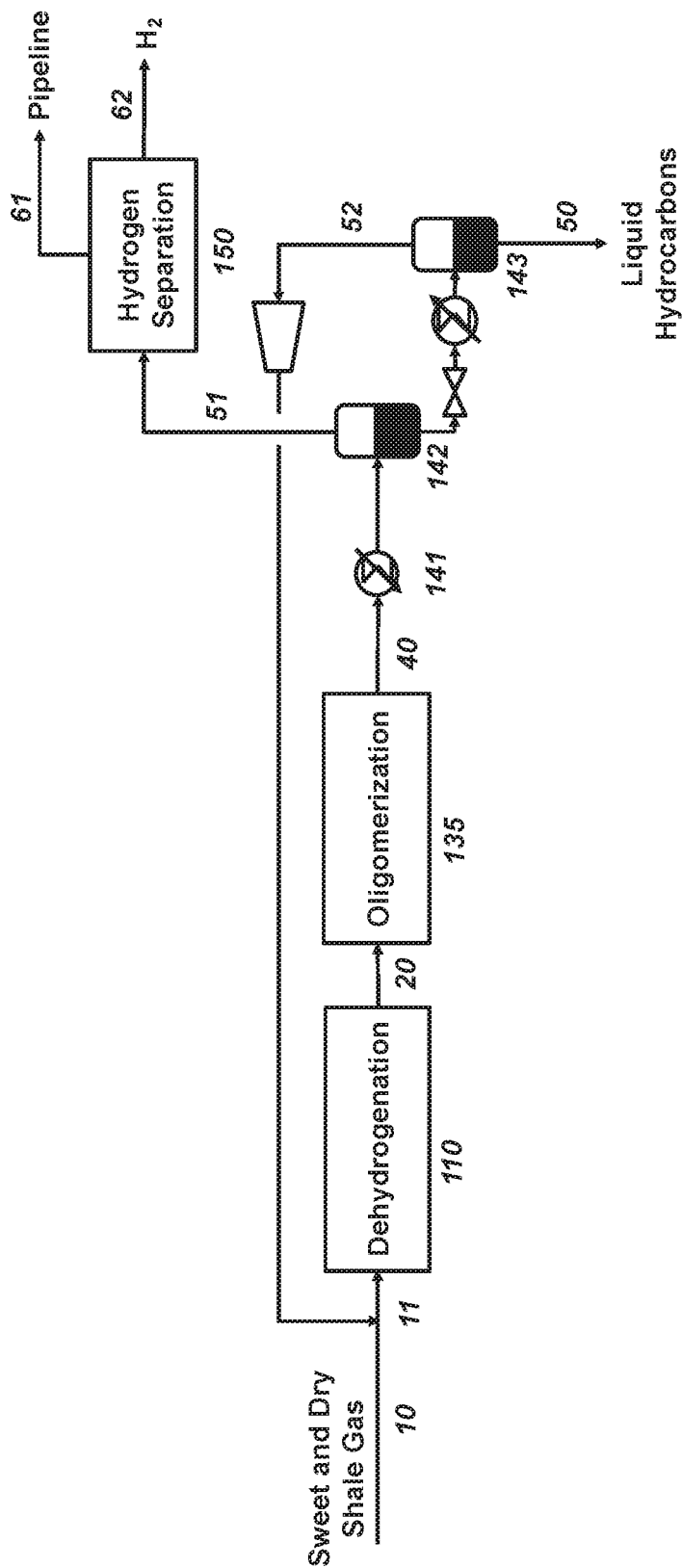
FIG. 11 depicts a flow diagram of another illustrative process where a hydrocarbon stream passes through a dehydrogenation reactor followed by an oligomerization reactor, the liquid hydrocarbons are recovered as product via a two-stage flash separation, the remaining gas stream is partially delivered to the pipeline after hydrogen is separated and a part of the gas is recycle to the dehydrogenation unit.

FIG. 11 depicts a flow diagram of yet another illustrative process, according to one or more embodiments provided herein. FIG. 11 provides an alternative process to that shown in FIGS. 9 and 10. As shown in FIG. 11, stream 51 exiting the flash separator 142 can be delivered to a hydrogen separation system 150 where hydrogen can be separated via stream 62. The hydrogen rich stream 62 can be acquired as hydrogen product or used as a fuel to provide heat to the dehydrogenation reactor 110, for example. The recovered hydrocarbon gases in stream 61 mainly contain methane and can be sent to a pipeline for distribution.

In the process schematics provided herein, all the needed compressors, expanders and heat exchangers are not explicitly shown. It is understood by those of ordinary skill in the art how and where to use such unit operations for the beneficial operation of the processes. As an example, consider the process in FIG. 9. A shale gas feed stream is essentially at a high pressure in excess of 20 bar. In such a case, the shale gas will have to be expanded to a lower pressure below 20 bar and preferably below 7 bar. The dehydrogenation reactor 110 generally operates at temperatures in excess 600° C. and preferably in excess of 700° C. For this purpose, a reactor has to be designed with appropriate heat exchangers to provide the needed heat to the reactor. On the other hand, an oligomerization reactor 135 operates at temperatures lower than 500° C. and preferably below 350° C. Therefore, stream 20 from the dehydrogenation reactor 110 can be cooled prior feeding it into the oligomerization reactor 135. Appropriate methods to recover heat of reaction from the oligomerization reactor 135 can be employed to improve efficiencies and costs. It is preferred to operate an oligomerization reactor 135 at pressures greater than 1 bar. Therefore, stream 20 from the dehydrogenation reactor can be compressed prior to feeding it to the oligomerization reactor 135. Similarly, in the hydrogen separation unit 150, stream 51 may be compressed to a higher pressure.

In any of the embodiments above or elsewhere herein, steam can be cofed to the dehydrogenation reactor 100. Even though it is not essential to co-feed steam to the dehydrogenation reactor 100, some steam could be mixed with the gas feed 10 prior to the dehydrogenation reactor 110. In such a case, a steam to NGL ratio can be much less than but no greater than a steam to ethane ratio used in the conventional steam-ethane cracker. Suitable steam to ethane ratios can vary from about 0.5 to about 0.85 kg steam per kg ethane. When steam is cofed to the dehydrogenation reactor 110, water can be separated at any suitable point during downstream processing.

In any of the embodiments above or elsewhere herein, the pressure of the gas feed 10 can be adjusted. If the pressure of the gas feed 10 is high, it can be expanded in an expander to the desired pressure while providing energy. This energy can be electrical energy, or the expander may be coupled to a compressor where expansion energy is used to compress the methane rich product stream (stream 31 or 61) from downstream processing to provide methane product at higher pressure. Generally, it will be beneficial to heat the gas feed 10 to a higher temperature using heat from one of the process streams prior to its expansion in the expander. On the other hand, the methane rich product stream 31 or 61 being compressed should be as close to ambient temperature as feasible prior to entering such compressor.

Examples

The foregoing discussion can be further described with reference to the following non-limiting examples.

Three process simulations are provided to illustrate the advantages of the embodiments shown and described with reference to FIG. 7 (dehydrogenation followed by methane separation followed by oligomerization) and FIG. 8 (dehydrogenation followed by hydrogen separation followed by oligomerization followed by methane separation) compared to the prior art process of FIG. 3 (methane separation followed by dehydrogenation followed by hydrogen separation followed by oligomerization). The process simulations are implemented by Aspen Plus. Table 5 below summarizes the simulated conversion results.

The feed information, including composition, flowrate, temperature and pressure, are the same for all three simulations. The methane separation unit in all three processes is modeled after an industrial standard single-stage demethanizer. The dehydrogenation reactors of all three processes are equilibrium reactors to reach the highest potential of alkane dehydrogenation at the reaction conditions. The oligomerization reactors of all three processes are also equilibrium reactors. The liquid hydrocarbon separation uses two-stage flash separation. The major stream information is given in the follow tables.

TABLE 2

Figure 3:
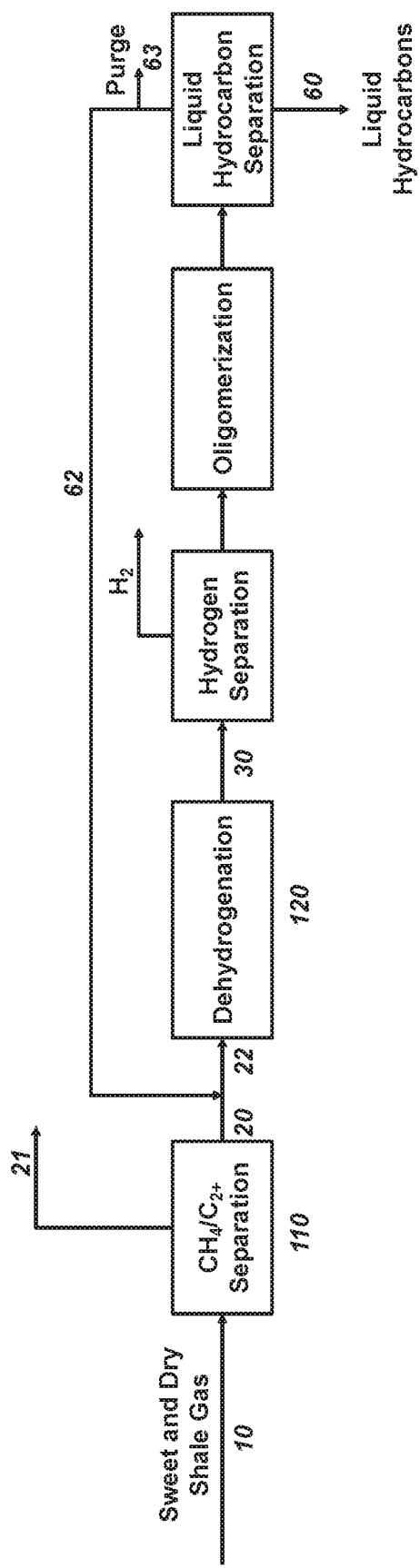
FIG. 3 is yet another block flow diagram showing the conventional processing steps (i.e. prior art) for converting natural gas liquids where a sweet and dry shale gas is first removed of methane and the separated NGLs are processed using a two-step catalytic dehydrogenation and oligomerization process for the production of liquid hydrocarbons.

Major stream information for the process of FIG. 3 (Comparative).

|  | Gas feed | Methane-rich stream | Dehydrogenation feed | Dehydrogenation out | Recycle Stream | Product Stream |
|---|---|---|---|---|---|---|
| Stream # | 10 | 21 | 22 | 20 | 62 | 50 |
| Temperature (° C.) | 50 | 108 | 800 | 800 | 35 | 22 |
| Pressure (bar) | 28.62 | 30.00 | 7.00 | 7.00 | 7.21 | 1.19 |
| Flowrate (kmol/h) | 4609.38 | 2922.04 | 6602.10 | 7913.34 | 4914.76 | 628.902 |
| Mole Fraction (%) |  |  |  |  |  |  |
| $N_2$ | 1.64 | 2.58 | 0.00 | 0.00 | 0.00 | 0.00 |
| $H_2$ | 0.00 | 0.00 | 14.32 | 28.52 | 19.24 | 0.00 |
| $CH_4$ | 60.36 | 91.28 | 20.78 | 17.34 | 25.58 | 0.01 |
| $C_{2+}$ alkanes | 38.00 | 6.14 | 51.50 | 26.39 | 37.18 | 21.11 |
| $C_{2+}$ alkenes | 0.00 | 0.00 | 13.40 | 27.75 | 18.00 | 78.88 |

Total conversion of $C_2$-$C_4$ alkanes to $C_{4+}$ alkenes is 73.45%.

TABLE 3

Major stream information for the process of FIG. 7.

|  | Gas Feed | Methane-rich stream | Dehydrogenation feed | Dehydrogenation out | Recycle stream | Product stream |
|---|---|---|---|---|---|---|
| Stream # | 10 | 31 | 11 | 20 | 52 | 50 |
| Temperature (° C.) | 706 | 116 | 800 | 800 | 38 | 22 |
| Pressure (bar) | 7.21 | 30.00 | 7.00 | 7.00 | 5.19 | 1.19 |
| Flowrate (kmol/h) | 4609.38 | 4541.48 | 6769.01 | 8352.29 | 2159.63 | 654.22 |
| Mole Fraction (%) |  |  |  |  |  |  |
| $N_2$ | 1.64 | 1.66 | 1.11 | 0.90 | 0.00 | 0.00 |
| $H_2$ | 0.00 | 34.86 | 0.00 | 18.96 | 0.00 | 0.00 |
| $CH_4$ | 60.36 | 61.26 | 44.36 | 35.95 | 10.20 | 0.01 |
| $C_{2+}$ alkanes | 38.00 | 0.71 | 48.24 | 20.13 | 70.10 | 20.87 |
| $C_{2+}$ alkenes | 0.00 | 1.51 | 6.29 | 24.06 | 19.70 | 79.12 |

Total conversion of $C_2$-$C_4$ alkanes to $C_{4+}$ alkenes is 88.27%.

TABLE 4

Major stream information for the process of FIG. 8.

|  | Gas Feed | Methane-rich stream | Dehydrogenation feed | Dehydrogenation out | Recycle stream | Product stream |
|---|---|---|---|---|---|---|
| Stream # | 10 | 61 | 11 | 20 | 62 | 50 |
| Temperature (° C.) | 706 | 112 | 800 | 800 | 45 | 22 |
| Pressure (bar) | 7.21 | 30.00 | 7.00 | 7.00 | 7.21 | 1.19 |
| Flowrate (kmol/h) | 4609.38 | 2799.71 | 6876.57 | 8294.38 | 2267.19 | 652.09 |
| Mole Fraction (%) | | | | | | |
| $N_2$ | 1.64 | 2.69 | 1.10 | 0.91 | 0.00 | 0.00 |
| $H_2$ | 0.00 | 18.90 | 0.00 | 17.09 | 0.00 | 0.00 |
| $CH_4$ | 60.36 | 77.43 | 43.51 | 36.08 | 9.27 | 0.03 |
| $C_{2+}$ alkanes | 38.00 | 0.87 | 42.58 | 18.21 | 51.90 | 20.27 |
| $C_{2+}$ alkenes | 0.00 | 0.11 | 12.81 | 27.71 | 38.83 | 79.70 |

Total conversion of $C_2$-$C_4$ alkanes to $C_{4+}$ alkenes is 75.77%.

TABLE 5

Summary of simulated results.

| Conversions (%) | FIG. 3 (Comparative Example) | FIG. 7 | FIG. 8 |
|---|---|---|---|
| Total conversion of $C_2$-$C_4$ alkanes to $C_{4+}$ alkenes | 73.45 | 88.27 | 75.77 |

From the results summarized in Table 5 above, the processes of FIGS. 7 and 8 can provide significantly higher overall conversions of $C_2$-$C_4$ alkanes in the feed gas to desired $C_{4+}$ liquid hydrocarbon products, as compared to the process scheme of FIG. 3. It was nothing short of surprising and unexpected to discover that these conversions could be obtained when upgrading NGLs in the presence of methane gas. Indeed, these simulations demonstrate the unexpected and significant benefits for dehydrogenating the gas feed prior to methane separation.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, meaning the values take into account experimental error, machine tolerances and other variations that would be expected by a person having ordinary skill in the art.

The foregoing has also outlined features of several embodiments so that those skilled in the art can better understand the present disclosure. Those skilled in the art should appreciate that they can readily use the present disclosure as a basis for designing or modifying other methods or devices for carrying out the same purposes and/or achieving the same advantages of the embodiments disclosed herein. Those skilled in the art should also realize that such equivalent constructions do not depart from the spirit and scope of the present disclosure, and that they can make various changes, substitutions, and alterations herein without departing from the spirit and scope of the present disclosure, and the scope thereof is determined by the claims that follow.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

What is claimed is:

1. A process for upgrading natural gas liquid (NGL) components, comprising:
   providing a hydrocarbon gas comprising at least 50 mol % methane and one or more other alkanes;
   at least partially dehydrogenating the hydrocarbon gas to produce a dehydrogenation effluent comprising the methane, hydrogen, one or more alkenes, and one or more unconverted other alkanes;
   separating the methane from the dehydrogenation effluent; and then
   recovering the one or more alkenes.

2. The process of claim 1, wherein the separated methane contains at least a portion of the hydrogen formed during dehydrogenation of the hydrocarbon gas.

3. The process of claim 2, further comprising separating at least a portion of the hydrogen from the separated methane to provide a hydrogen-rich stream.

4. The process of claim 1, further comprising separating the one or more unconverted other alkanes from the dehydrogenated effluent and recycling the separated one or more unconverted other alkanes to the hydrocarbon gas.

5. The process of claim 1, wherein the at least partially dehydrogenating the hydrocarbon gas takes place in a reactor comprising one or more catalyst beds to catalytically convert the alkanes to their respective alkene derivatives.

6. The process of claim 1, further comprising at least partially oligomerizing the one or more alkenes in the dehydrogenation effluent to provide an oligomerization effluent comprising the one or more unconverted other alkanes and one or more C4 to C26 oligomers.

7. A process for upgrading natural gas liquid (NGL) components, comprising:

providing a hydrocarbon gas feed comprising acid gas, water, methane and one or more other alkanes;

removing at least a portion of the acid gas and water to provide a treated gas having concentrations of acid gas and water within a desired range for downstream processing;

at least partially dehydrogenating the treated gas to produce a dehydrogenation effluent comprising the methane, hydrogen, one or more alkenes, and one or more unconverted other alkanes;

separating methane from the dehydrogenation effluent; and then recovering the one or more alkenes.

8. The process of claim 7, wherein the separated methane contains at least a portion of the hydrogen formed during dehydrogenation of the hydrocarbon gas.

9. The process of claim 8, further comprising separating at least a portion of the hydrogen from the separated methane to provide a hydrogen-rich stream.

10. The process of claim 9, further comprising separating the one or more unconverted other alkanes from the dehydrogenated effluent and recycling the separated one or more alkanes to the treated gas.

11. The process of claim 7, wherein at least partially dehydrogenating the treated gas takes place in a reactor comprising one or more catalyst beds to catalytically convert the alkanes to their respective alkene derivatives.

12. The process of claim 7, wherein the one or more other alkanes comprise one or more natural gas liquids.

13. A process for upgrading natural gas liquid (NGL) components, comprising:

providing a hydrocarbon gas comprising at least 50 mol % methane and one or more natural gas liquids comprising $C_{2+}$ hydrocarbons;

at least partially dehydrogenating the one or more natural gas liquids in the hydrocarbon gas to provide a dehydrogenation effluent comprising the methane, hydrogen, one or more C2+ olefins, and one or more unconverted other alkanes;

at least partially oligomerizing the one or more $C_{2+}$ olefins in the dehydrogenation effluent to provide an oligomerization effluent comprising the methane, the one or more unconverted other alkanes and $C_4$ to $C_{26}$ oligomers; and then separating the methane from the oligomers.

14. The process of claim 13, further comprising at least partially separating hydrogen from the dehydrogenation effluent prior to at least partially oligomerizing the one or more $C_{2+}$ olefins.

15. The process of claim 13, further comprising separating the one or more unconverted other alkanes from the methane and recycling the separated one or more unconverted other alkanes to the hydrocarbon gas.

16. The process of claim 13, further comprising recovering the oligomers as a liquid hydrocarbon product.

17. The process of claim 13, further comprising at least partially separating hydrogen from the methane.

18. The process of claim 13, further comprising separating the one or more unconverted other alkanes from the oligomers.

19. The process of claim 18, further comprising recycling the separated one or more alkanes to the hydrocarbon gas.

20. The process of claim 13, wherein the hydrocarbon gas is derived from shale gas or the hydrocarbon gas is a sweet and dry natural gas.

* * * * *